US006713058B2

(12) United States Patent
McMichael

(10) Patent No.: US 6,713,058 B2
(45) Date of Patent: *Mar. 30, 2004

(54) METHODS FOR ALLEVIATING SYMPTOMS ASSOCIATED WITH NEUROPATHIC CONDITIONS COMPRISING ADMINISTRATION OF LOW LEVELS OF ANTIBODIES

(75) Inventor: John McMichael, Delanson, NY (US)

(73) Assignee: Milkhaus Laboratory, Inc., Delanson, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/223,498

(22) Filed: Aug. 19, 2002

(65) Prior Publication Data

US 2003/0035803 A1 Feb. 20, 2003

Related U.S. Application Data

(63) Continuation-in-part of application No. 09/918,343, filed on Jul. 30, 2001, now Pat. No. 6,436,401, which is a continuation-in-part of application No. 09/774,770, filed on Jan. 31, 2001, now Pat. No. 6,294,171, which is a continuation-in-part of application No. 09/514,993, filed on Feb. 29, 2000, now Pat. No. 6,187,309.
(60) Provisional application No. 60/153,838, filed on Sep. 14, 1999.

(51) Int. Cl.$^7$ ............................................. A61K 39/395
(52) U.S. Cl. ................................. 424/145.1; 424/146.1
(58) Field of Search ............................ 424/145.1, 146.1

(56) References Cited

U.S. PATENT DOCUMENTS

| | | | |
|---|---|---|---|
| 4,384,993 A | 5/1983 | Sato et al. | |
| 4,692,331 A | 9/1987 | Uemura et al. | |
| 5,645,998 A | 7/1997 | Atkinson et al. | |
| 5,762,937 A | 6/1998 | Atkinson et al. | |
| 5,792,620 A | 8/1998 | Lernmark et al. | |
| 6,001,360 A | 12/1999 | Atkinson et al. | |
| 6,011,139 A | 1/2000 | Tobin et al. | |
| 6,025,176 A | 2/2000 | Lernmark et al. | |
| 6,187,309 B1 | 2/2001 | McMichael et al. | |
| 6,294,171 B2 | 9/2001 | McMichael | |
| 6,300,089 B1 | 10/2001 | Atkinson et al. | |
| 6,436,401 B1 * | 8/2002 | McMichael | 424/145.1 |

FOREIGN PATENT DOCUMENTS

| | | |
|---|---|---|
| CA | 2232834 | 3/1997 |
| WO | WO 92/20811 | 11/1992 |
| WO | WO 97/10847 | 3/1997 |

OTHER PUBLICATIONS

Blanas et al., "Induction of Autoimmune Diabetes by Oral Administration of Autoantigen," *Science*, 274:1707–1709 (1996).

Graves et al., "Lack of Association Between Early Childhood Immunizations and β–Cell Autoimmunity," *Diabetes Care*, 22:1694–1697 (1999).

Kaufman et al., "Spontaneous Loss of T–Cell Tolerance to Glutamic Acid Decarboxylase in Murine Insulin–Dependent Diabetes," *Nature*, 366: 69–72(1993).

Tian et al., "Modulating Autoimmune Responses to GAD Inhibits Disease Progression and Prolongs Islet Graft Survival in Diabetes–Prone Mice," *Nat. Med.*, 2:1348–1353 (1996).

Tisch et al., "Immune Response to Glutamic Acid Decarboxylase Correlates with Insulitis in Non–Obese Diabetic Mice," *Nature*, 366:72–75 (1993).

Ramiya et al., "Effect of Oral and Intravenous Insulin and Glutamic Acid Decarboxylase in NOD Mice," *Autoimmunity*, 26:139–151 (1997).

Song et al., "Human Insulin B Chain but not A Chain Decreases the Rate of Diabetes in BB Rats," *Diabetes Research and Clinical Practice*, 46:109–114 (1999).

Asperger, "Die Psychopathologie des Coeliakakranken kindes," Ann. Pediatr., 197:346–351 (1961).

Barker et al., "A Role for Complement in the Rejection of Porcine Ventral Mesencephalic Xenografts in a Rat Model of Parkinson's Disease," *J. of Neuroscience*, 20:3415–3424 (2000).

DiFiglia et al., "Aggregation of Huntingtin in Neuronal Intranuclear Inclusions and Dystrophic Neurites in Brain," *Science*, 277:19901993 (1998).

Dirkx et al., "Targeting of the 65–kDa Isoform of Glutamic Acid Decarboxylase to Intracellular Organelles is Mediated by Its Interaction with the $NH_2$–terminal Region of the 65–kDa Isoform of Glutamic Acid Decarboxylase," *J. Biol. Chem*, 270:2241–2246 (1995).

Fahn et al., "Double–Blind Controlled Trial of Human Embryonic Dopaminergic Tissue Transplants in Advanced Parkinson's Disease: Clinical Outcomes," *Neurology*, 52:A405 (1999).

Heiser et al., "Inhibition of Huntingtin Fibrillogenesis by Specific Antibodies and Small Molecules: Implications for Huntington's Disease Therapy," *Proc. Natl. Acad. Sci. USA*, 97:6739–6744 (2000).

Kopyov et al., "Safety of Intrastriatal Neurotransplantation for Huntington's Disease Patients," *Exp. Neurol.*, 149:97–108 (1998).

(List continued on next page.)

Primary Examiner—Raymond Henley, III
(74) Attorney, Agent, or Firm—Marshall, Gerstein, & Borun LLP

(57) ABSTRACT

The invention provides methods and compositions for alleviating the symptoms of neuropathic conditions with a pharmaceutical composition including an effective amount of anti-glutamic acid decarboxylase (anti-GAD) antibodies.

20 Claims, No Drawings

Kordower et al., "Intravenous Administration of a Transferrin Receptor Antibody–nerve Growth Factor Conjugate Prevents the Degeneration of Cholinergic Striatal Neurons in a Model of Huntington Disease," *Proc. Natl. Acad. Sci. USA*, 91:9077–9080 (1994).

Lecerf et al., "Human Single–chain Fv Intrabodies Counteract in situ Huntintin Aggregation in Cellular Models of Huntington's Disease," *Proc. Natl. Acad. Sci. USA.*, 98:4764–4769 (2001).

Martin et al., "Regulatory Properties of Brain Glutamate Decarboxylase (GAD): The Apoenzyme of GAD is Present Principally as the Smaller of Two Molecular Forms of GAD in Brain," *J. Neuroscience*, 11:2725–2731 (1991).

Namchuck et al., "Phosphorylation of Serine Residues 3, 6, 10, and 13 Distinguishes Membrane Anchored from Soluble Glutamic Acid Decarboxylase 65 and is Restricted to Glutamic Acid Decarboxylase 65α*," *J. Biol. Chem.*, 272:1548–1557 (1997).

Peltola et al., "No Evidence for Measles, Mumps, and Rubella Vaccine–Associated Inflammatory Bowel Disease or Autism in a 14–Year Prospective Study," *Lancet*, 351:1327–1328 (1998).

Porter et al., "Transaminations Catalysed by Brain Glutamate Decarboxylase," *Biochem J.*, 231:705–712 (1985).

Qu et al., "Motifs and Structural Fold of the Cofactor Binding Site of Human Glutamate Decarboxylase," *Protein Science*, 7:1092–1105 (1998).

Comi et al., "Familial Clustering of Autoimmune Disorders and Evaluation of Medical Risk Factors in Autism," *J. of Child Neurology*, 14:388–394 (1999).

Wakefield et al., "Ileal–lymphoid–nodular Hyperplasia, Non–specific Colitis, and Pervasive Development Disorder in Children," *Lancet*, 351:637–641 (1998).

Walker–Smith et al. ,"Alpha–1–Antitrypsin, Autism, and Coeliac Diseae," *Lancet, ii*:883–884 (1972).

D'Eufemia et al., "Abnormal Intestinal Permeability in Children with Autism," *Acta Paediatrica*, 85:1076–1079 (1996).

Warren et al., "Elevated Serotonin Levels in Autism: Association with the Major Histocompatibility Complex," *Neuropsychobiology*, 34:72–75 (1996).

Weiss, R.A., "Xenografts and Retroviruses," *Science*, 285:1221–1222(1999).

* cited by examiner

METHODS FOR ALLEVIATING SYMPTOMS ASSOCIATED WITH NEUROPATHIC CONDITIONS COMPRISING ADMINISTRATION OF LOW LEVELS OF ANTIBODIES

This application is a continuation-in-part of U.S. application Ser. No 09/918,343 filed Jul. 30, 2001 and issued Aug. 20, 2002 as U.S. Pat. No. 6,436,401, which is a continuation-in-part of U.S. application Ser. No. 09/774,770 filed on Jan. 31, 2001 and issued Sep. 25, 2001 as U.S. Pat. No. 6,294,171, which is a continuation-in-part of U.S. application Ser. No. 09/514,993 filed on Feb. 29, 2000 and issued Feb. 13, 2001 as U.S. Pat. No. 6,187,309, which claims benefit of U.S. Provisional Application Serial No. 60/153,838 filed on Sep. 14, 1999; the disclosures of which are hereby incorporated by reference.

BACKGROUND OF THE INVENTION

The therapeutic use of antibodies is generally limited to: (a) immunotherapy, where a specific antibody directed against a discreet antigen is used to counter the effect of that antigen, e.g., using an antitoxin administered to neutralize a toxin, or antibody against an infectious agent to interrupt the pathophysiological process induced by that target organism; (b) the administration, often i.v., of high levels of antibody (gamma globulin therapy) to compensate for transient or permanent immune deficiency; and (c) monoclonal antibody therapy to combat cancer, certain autoimmune disorders, metabolic diseases, and symptoms associated with neuropathic conditions. In all these cases, antibody is provided in relatively high concentrations for the purpose of having that antibody combine directly with its target antigen to render that antigen inoperable, non-infectious or neutralized. For example, Gamimune™ (Bayer Biological) contains 50 mg protein (immunoglobin) per mL and normal dosing can be up to 1000 mg/kg body weight. Gammar—P™ I.V. (Aventis Behring) is administered at dosages up to 400 mg/kg body weight. Bayhep B™ (Hepatitis B Immunoglobulin) (Bayer Biological) is 15–18% protein [immunoglobulin] is administered at dosages of up to 0.6 ml/kg body weight=0.01 g/kg=100 mg/kg. Further, Imogam Rabies—HT™ (Aventis Pasteur) is 10–18% protein and is administered at a dosage of 0.133 ml/kg (240 mg/kg) body weight.

Diabetes mellitus is a metabolic disease state that is caused by a deficiency of insulin (Type I diabetes) or by the body's resistance to diabetes (Type II diabetes). The disease is characterized by chronic hyperglycemia, glycosuria, water and electrolyte loss, ketoacidosis, neuropathy, retinopathy, nephropathy, increased susceptibility to infection, and coma. Type I diabetes results from the autoimmune destruction of beta cells of the pancreas. Thus, proteins produced by beta cells have been a prime target in the study of diabetes as potential autoantigens that serve as the target for the immune response against the beta cells. One autoantigen found to correspond to the onset of Type I diabetes is glutamic acid decarboxylase (GAD) [Tisch, Roland, et al., *Nature* 366:72–75 (1993)]. Another example of a beta cell autoantigen is insulin.

Much of the research involving the autoimmune response against beta cells or the autoantigens thought to be involved in the autoimmune response has included the administration of autoantigens, immunogenic portions of autoantigens, or molecules that mimic the autoantigens. Tian, Jide, et al., *Nat Med* 2(12): 1348–53 (1996) discusses administration of GAD to alter the diverse immune response that can lead to diabetes. Ramiya, Vijayakumar K., et al., *Autoimmunity* 26:139–151 (1997) discussed administration of insulin and GAD in non-obese diabetic mouse to achieve anti-diabetic affects.

Glutamate decarboxylase (hereafter GAD) is the pyridoxal-5'-phosphate dependent enzyme that synthesizes gamma-aminobutyric acid (GABA), the major inhibitory neurotransmitter in vertebrate brain (Qu et al., *Protein Science* 7:1092–1105 (1998)). Glutamic acid decarboxylase is of two types, GAD-65, which is highest in concentrations in the pancreas, and GAD-67, which is highest in concentration in the central nervous system. Each GAD is composed of two major domains: a C-terminal domain of about 500 amino acids, and a 95–100 amino acid n-terminal domain. The C-terminal domain contains the pyridoxal-P binding site and lengthy segments that have identical sequences in GAD-65 and GAD-67. The amino terminal domain of GAD targets membranes and forms heteromultimers of GAD-65 and GAD-67 (Dirkx et al., *J. Biol. Chem.* 270:2241–2246 (1995)). Phosphorylation sites have been found in GAD-65 (Namchuck et al., *J. Biol. Chem.* 272:1548–1557 (1997)). Pyridoxal-P plays a key role in the regulation of GAD activity. GAD is unusual, if not unique, among pyridoxal-P-dependent enzymes in the brain because it is present mainly in an inactive apoenzyme (GAD without bound pyridoxal-P) (Martin et al., *J. Neuroscience* 11:2725–2731 (1991)). This apoGAD serves as a reservoir of inactive enzymes that can be converted to active holoGAD when additional GABA synethesis is required (Porter et al., *Biochem. J.* 231:705–712 (1985)). The invention disclosed herein found treatment with GAD-65 antibody was most effective but not limited to treating patients suffering from diabetes while treatment with GAD-67 antibody was most effective but not limited to treating patients suffering from CNS disorders such as but not limited to multiple sclerosis, autism, Parkinson's disease, and pain related neuropathy.

Of interest to the present application is the disclosure of co-owned U.S. Pat. No. 6,187,309, which is directed to the administration of anti-rubella antibodies for the treatment of symptoms of various central nervous system diseases including autism, multiple sclerosis, attention deficit disorder (ADD) and attention deficit hyperactivity disorder (ADHD). Examples therein demonstrated the efficacy of treating the symptoms of those disease states with dosages of from 0.1 mg to 1 mg of anti-rubella antibody per dose.

Autism is a complex developmental disorder that appears in the first 3 years of life. It affects the brain's normal development of social and communication skills. Autism is a spectrum that encompasses a wide continuum of behavior. Core features included impaired social interactions, impaired verbal and nonverbal communication, and restricted and repetitive patterns of behavior. The symptoms may vary from quite mild to quite severe. Autisms is a physical condition linked to abnormal biology and neurochemistry possibly linked to autoimmune disorder of type 1 diabetes and the autoantigen GAD.

The most distinctive feature of autistic children is that they appear isolated from the world around them and may appear detached, aloof, or in a dreamlike world. Autistic children often appear only vaguely aware of others in their environment, including family members, and frequently display unusual mannerisms and engage in ritualistic behavior. Appropriate play with other children or toys is uncommon and there is often a great interest in inanimate objects, especially mechanical devices and appliances. In many cases the disorder is evident during the first 30 months of life. Autistic children are normal in appearance, physically well developed and are usually boys (by a ratio of 3:1). Historically, children were frequently institutionalized by the ages of nine or ten because their parents were no longer able to control them. While, the availability and effectiveness of behavioral support services and advances in treatment and education of treatment of children with autism have reversed the trend toward institutionalization autistic children still require significant resources for their care.

There are no medical tests that can be used to determine autism. Instead, the diagnosis of autism is made when a subject displays six of 12 characteristic behaviors that match the criteria in the Diagnostic and Statistical Manual, Fourth Edition (DSM IV), published by the American Psychiatric Association. Subjects with autism, compared to other disabled persons of commensurate ability, are more difficult to teach and comparatively have significantly greater problems acquiring and using language and relating socially. Historically, about 75 percent of subjects with autism are classified as mentally retarded.

Autism was first described by Dr. Leo Kanner, a psychiatrist at John Hopkins University in the 1940's who examined a group of 11 children who were self-absorbed and who had severe social, communication, and behavioral problems. It was originally believed that subjects with autism had good cognitive potentialities and that autistic children possessed latent genius that could be unlocked by discovery of the appropriate key for that child. Associated with that belief was the misconception that autism was caused by parent's behavior and particularly was the result of "cold" mothers whose projection of hopelessness, despair and apathy was projected onto their children. More recently, this psychoanalytic view of autism was replaced by a neurologically based approach and continuing study as to the organic causes of the disease. Of interest to the present invention is the observation that the incidence of autism may be increasing in the population in the United States and other developed countries. In a recent report to the state legislature, the California Department of Developmental Services has described a three-fold increase in the number of persons with autism statewide between 1987 and 1998 and a doubling of the percentage of total mental health client population accounted for by persons with autism during that time. Similar observations have been made elsewhere in the United States and in other developed countries.

Much speculation concerning the apparent increase in the incidence of autism has focused on possible links between immunological causes of the disease. Prenatal and postnatal infections have been implicated as possible causes of autism. In particular, congenital rubella and HSV infections have been associated with incidence of autism.

Links between a family history of autoimmune disorders such as type 1 diabetes, adult rheumatoid arthritis, hypothroidism and systemic lupus erythematosus have also been observed with the occurrence of autism suggesting that immune dysfunction may interact with various environmental factors to play a role in autism pathogenesis. *Journal of Child Neurology*, vol. 14, number 6 pp. 388–394 (June 1999).

Other workers have reported an association between autism and the presence of antibodies against human herpes virus-6, as well as autoantibodies against tissues of the central nervous system such as myelin basic protein (MBP). See Warren et al. *Neuropsycholobiology* 34:72–75 (1996).

In addition, Asperger, "Die Pyschopathologie des coeliakakranken kindes." *Ann, Pediatr.* 197: 146–151 (1961) reported an association between intestinal dysfunction and autism. Other studies including those of Walker-Smith et al. *Lancet* ii: 883–84 (1972) and *D'Eufemia Acta Paediatrica* 85: 1076–79 (1996) which show low concentrations of alpha-1 anti-trypsin and abnormal intestinal permeability respectively suggest that the consequences of an inflamed or dysfunctional intestine may play a part in behavioral changes in some patients.

Recently, attention has focused on the possibility of an association between childhood vaccinations and autism. Both, infection and the immune reaction resulting from immunization would be consistent with an immunological cause of the disease. In particular, the combined measles, mumps, and rubella (MMR) vaccine, rather than the monovalent measles vaccine, has been associated with the onset of autism. See Gupta *Proc. Natl. Autism Assn.* Chicago 1996, 455–460. This observation has led to the suggestion that some form of immune overload may constitute an aspect of susceptibility to measles vaccination. As a consequence, some workers in the field have suggested a suspension of administration of the combined MMR vaccine in favor of sequential administration over time of the three vaccine components.

Wakefield et al. *Lancet* 351: 637–641 (1998) identified a chronic enterocolitis in children related to neuropsychiactric dysfunction and autism. In most cases, the onset of symptoms occurred after immunization with the MMR vaccine. While Wakefield et al. stated that they had not proven an association between MMR vaccine and the syndrome described they suggested that ongoing virological and epidemiological studies might resolve the issue. At that time, Wakefield et al. suggested that the published evidence was inadequate to show whether there was a change in incidence or a link with MMR vaccine. But see, Peltola, et al. *Lancet* 351:1327–1328 (1998) which reported work in which children who received the MMR vaccination in Finland between 1982 and 1996 were traced but failed to find support for the suggestion that the vaccination could cause autism or bowel disease. Additional work by Wakefield and others indicates that there exists live measles (rubella) vaccine virus in the guts of the vast majority of autistic children and that autistic patients often have a serum antibody titer to rubella virus hundreds of times higher than normal, suggesting continual or oft-repeated exposure and/or incomplete or failed elimination of the virus by the human response. Significantly, if rubella virus were present in the gut, as suggested by photomicrographs by Wakefield, such virus particles would be protected from the body's immune defenses because antibodies do not generally travel from the circulatory system to the lumen of the intestinal tract. Accordingly, massive numbers of circulating antibodies may be of no real protective value against rubella virus in the gut.

While the possibility of a link between MMR vaccination and autism has prompted suggestions that measles vaccine be applied singly rather than as a component of a multi-component vaccine as a means for reducing the incidence of autism there remains a need for method of treating the symptoms of autism in subjects who already affected by the condition.

Multiple sclerosis (MS) is a slowly progressing demyelinating disease of the central nervous system which is insidious and characterized by multiple and varied neurological symptoms characterized by remissions and exacerbations. These repeated episodes of inflammation of the nervous tissue generally occur in the area of the central nervous system like the brain and spinal cord. The location of the inflammation varies from person to person and from episode to episode. The inflammation destroys the covering of the nerve cells in that area (myelin sheath), leaving multiple areas of scar tissue (sclerosis) along the covering of the nerve cells. This results in slowing or blocking the transmission of nerve impulses in that area, leading to the symptoms of multiple sclerosis. Symptoms vary because the location and extent of each attack varies. There is usually a stepwise progression of the disorder, with episodes that last days, weeks, or months alternating with times of reduced or no symptoms (remission). The onset of the disease usually occurs between 20 and 50 years of age with a peak occurring in people 30 years old. MS is believed to be immunological in nature but treatment with immuno-suppressive agents is not advised. The prevalence of MS varies widely with location with the highest prevalence found at higher latitudes in northern Europe and northern North America. The geographic variation suggests that MS may in part be caused by the action of some environmental factor that is more common in high latitudes.

Symptoms of multiple sclerosis include, but are not limited to, weakness of one or more extremities, paralysis of one or more extremities, tremors of one or more extremities, muscle spasticity, muscle atrophy, dysfunctional movement beginning in the legs, numbness, tingling, facial pain, loss of vision, double vision, eye discomfort, rapid eye movements, decreased coordination, loss of balance, dizziness, vertigo, urinary hesitancy, strong urge to urinate, frequent need to urinate, decreased memory, decreased spontaneity, decreased judgment, loss of ability to think abstractly, depression, decreased attention span, slurred speech, and fatigue. Symptoms vary with each attack. They may last days to months, then reduce or disappear, then reoccur periodically.

There is no known cure for multiple sclerosis. There are, however, promising new therapies that may decrease exacerbations and delay progression of the disease. Treatment is aimed at controlling symptoms and maintaining function to give the maximum quality of life. Patients with a relapsing-remitting course are now placed on immune modulating therapy that requires injection under the skin or in the muscle once or several times a week. This treatment is in the form of interferon (such as Avonex or Betaseron) or another medicine called glatiramer acetate (Copaxone). Other than protective therapies, steroids are given to decrease the severity of an attack if it occurs. Other medicines include Baclofen, Tizanidine, or Diazepammay may be used to reduce muscle spasticity. Cholinergic medications may be helpful to reduce urinary problems. Antidepressant medications may be helpful for mood or behavior symptoms. Amantadine may be given for fatigue. There is a need, however, in the art for more effective treatment for multiple sclerosis.

Huntington's disease is an inherited condition characterized by abnormal body movements, dementia, and psychiatric problems. This progressive disease involves wasting (degeneration) of nerve cells in the brain. Huntington's disease is inherited as a single faulty gene on chromosome #4. There is a part of the gene that is repeated in multiple copies. The greater number of repeats, the more likely it is that the person will develop symptoms and the greater the chance they will occur at a younger age. The disease may occur earlier and more severely in each succeeding affected generation because the number of repeats can increase.

The molecular mechanisms responsible for delayed onset, selective pattern of neuropathology, and cell death in Huntington's disease is unknown. However, insoluble huntington protein aggregates have been detected in an in vitro model system as well as in transgenic animals, fly models, cell culture systems, and brains of Huntington disease patients (DiFiglia et al., *Science* 277:1990–1993 (1998)). This study demonstrated that mAb 1C2 as well as the chemical compounds Congo red, thioflavine S, Direct fast yellow, and chrysamine G are capable of preventing Huntington aggregation in vitro, at least partially (Id., at 6743). Another antibody treatment method that is being developed is using intracellular intrabodies as a means of blocking the pathogenesis of Huntington's disease (Lecerf et al., *Proc. Natl. Acad. Sci. USA* 98:4764–4769 (2001)).

Symptoms do not usually appear until adulthood, typically between ages 35 and 50 years old, but this depends on the number of repeats found in the gene so it may appear in younger people as well. In children, symptoms may appear to be Parkinson's Disease with rigidity, slow movements, and tremors. There is a progressive loss of mental function, including personality changes, and loss of cognitive functions such as judgment and speech. Abnormal facial and body movements develop, including jerking movements. Symptoms of the disease also include irritability, restlessness, antisocial behavior, psychosis, paranoia, hallucinations, facial movements, progressive dementia, loss of memory, loss of judgment, speech changes, loss of other functions, personality changes, disorientation and confusion, unsteady gait, abnormal (choreiform) movements including jerking movements of the arms, legs, face, and trunk, speech impairment, anxiety, stress, tension and difficulty in swallowing.

There is no cure for Huntington's disease and there is no known way to stop progression of the disorder. Genetic counseling is advised if there is a family history of Huntington's disease. This may include DNA analysis of multiple family members. Treatment is aimed at slowing progression and maximizing ability to function for as long as possible. Medications vary depending on the symptoms. Dopamine blockers such as haloperidol or phenothiazine medications may reduce abnormal behaviors and movements. Reserpine and other medications have been used, with varying success. Drugs like Tetrabenazine and Amantidine are used to try to control extra movements. There has been some evidence to suggest that Co-Enzyme Q10 may minimally decrease progression of the disease.

Alternative therapies such as using antibodies to treat Huntington's disease began when antibodies directed against the transferring receptor (OX-26) were fused to nerve growth factor. This preventative fusion neurotrophic factor-antibody conjugate was shown to prevent degeneration of central nerve growth factor responsive neurons following systemic administration (Kordower et al., *Proc. Natl. Acad. Sci.* 91:9077–9080 (1994). Other antibodies that may prevent neuron degeneration include the antibody 1C2, which selectively recognizes elongated polyQ chains which suppresses the aggregation of HD exon 1 protein (Heiser et al., *Proc. Natl. Acad. Sci.* 97:6739–6744 (2000)). In addition, the use of intracellular antibodies (intrabodies) has helped to better understand the mechanisms of Huntingtons disease. For example, intrabodies have been developed wherein they target the 17 N-terminal residue of the huntingtin protein, adjacent to the polyglutamine in HD exon 1. This interaction suggests intrabody-mediated modulation of abnormal neuronal proteins may contribute to the treatment of neurodegenerative diseases such as Huntington disease, Alzheimer's, Parkinson's, prion disease, and the spinocerebellar ataxis (Lecerf et al., *Proc. Natl. Acad. Sci.* 98:4764–4769 (2001)). However, these treatments are just in their experimental stages, are designed to prevent further wasting of neurons, and only provide a small amount of insight into the possible pathology of Huntington's disease. Therefore, there is a need in the art for alternative therapies that provide effective treatment of Huntington's disease.

Parkinson's disease is a disorder of the brain characterized by shaking and difficulty with walking, movement, and coordination. The disease is associated with damage to a part of the brain that is involved in the execution of movement. Parkinson's disease affects approximately 2 out 1000 people, and most often develops after age 50. It does occasionally occur in younger adults and rarely in children. It affects both men and women and is one of the most common neurologic disorders of the elderly. In some cases, the disease occurs within families, especially when it affects young people. Most late onset cases are sporadic. The term "parkinsonism" refers to any condition that involves a combination of the types of changes in movement seen in Parkinson's disease, which happens to be the most common condition causing this group of symptoms. Parkinsonism may be caused by other disorders or by external factors.

Parkinson's disease is caused by progressive deterioration of the nerve cells of the part of the brain that controls muscle movement (the basal ganglia and the extra pyramidal area). Dopamine, which is one of the substances used by cells to transmit impulses (transmitters), is normally produced in this area. Deterioration of this area of the brain reduces the amount of dopamine available to the body. Insufficient dopamine disturbs the balance between dopamine and other transmitters, such as acetylcholine. Without dopamine, the nerve cells cannot properly transmit messages, and this result in the loss of muscle function. The exact reason that the cells of the brain deteriorate is unknown. The disorder may affect one or both sides of the body, with varying degrees of loss of function. Depression also accompanies this disease due to the person's slow loss of muscle function. Symptoms include muscle rigidity, loss of balance, shuffling walk, slow movements, difficulty beginning to walk, freezing of movement, muscle aches, shaking and tremors, changes in facial expression, voice/speech changes, and loss of fine motor skills, frequent falls, and decline in intellectual function.

There is no known cure for Parkinson's disease. Treatment is aimed at controlling the symptoms. Medications control symptoms primarily by controlling the imbalance of transmitters. Many of the current medications require monitoring due to severe side effects. Deprenyl may provide some improvements to mildly affected patients. Amantadine and/or anticholinergic medications may be used to reduce early or mild tremors. Levodopa is a medication that the body converts to dopamine. It may be used to increase the body's supply of dopamine, which may improve balance and movement. Carbidopa is a medication that reduces the side effects of Levodopa and makes Levodopa work well. Additional medications that reduce symptoms and control side effects of primary treatment medications include antihistamines, antidepressants, dopamine agonists, monoamine oxidase inhibitors, and others. One alternative treatment in the experimental stage is allotransplantation of embryonic neural tissue into the disease CNS. Good clinical results have been shown for Parkinson's disease (Fahn et al., *Neurology* 52 [Suppl 2]:A405; Kopyov et al., *Exp. Neurol.* 149:97–108 (1998)). Problems with this alternative treatment are xenografts are rejected and the ethical issues of using suitable donor tissues. The use of embryonic neural tissue from pig has been experimented and offers their own problems of zoonotic infection as well as rejection (Weiss, R. A., *Science* 285:1221–1222 (1999)). The role of complement appears to be a major player in porcine tissue rejection (Baker et al., *J. of Neuroscience* 20:3415–3424 (2000)). Therefore, due the present state of treatment of Parkinson's wherein the medications either entail many side effects or the use of grafts is still in its infancy, there is a need in the art for more effective treatment for Parkinson's disease.

Attention Deficit Disorder (ADD) is the most commonly diagnosed psychological disorder of childhood, affecting 3% to 5% of school aged children. Symptoms include developmentally inappropriate levels of attention, concentration, activity, distractibility, and impulsivity. There are three sub-categories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type. Despite much progress in the diagnosis and treatment of ADD, the treatment for this disorder remains highly controversial. While the cause of attention deficit disorder is unknown, scientists have determined a neurological basis for the disease and genes have been identified that are thought to be involved in ADD.

The most effective treatment strategy for ADD is using psychotropic medications such as Dexedine (dextroamphetamine), Ritalin (methylphenidate), and Cylert (magnesium pemoline). Antidepressants (such as amitriptyline or fluoxetine), tranquilizers (such as thioridazine), alpha-adrenergic agonist (clonidine), and caffeine have also been tried to treat ADD. The disadvantage of these drugs is the lack of long term information on the affect these drugs have on the cognitive and emotional development of ADD children. In addition, medications such as antidepressants, tranquilizers, and caffeine have met with little success. A significant amount of research has been carried out studying psychological therapeutic treatments such as contingency management (e.g. time out), cognitive-behavioral treatment (e.g. self monitoring, verbal self instruction, problem solving strategies, and self reinforcement), parent counseling, and individual psychotherapy. Studies using these techniques have yielded mixed results and no studies have been carried out combining psychological interventions with stimulant medications. Therefore, parents are directed to manage the symptoms and direct the child's energy to constructive and educational paths.

While the administration of larger quantities of immunoglobulins is effective in the treatment of many disease states, there remains a desire in the art for methods for the treatment and prevention of diabetes, or neuropathic disorders such as autism, multiple sclerosis, Huntington's disease, Parkinson's disease, attention deficit disorder, diabetes neuropathy, and pain neuropathy following chemotherapy.

SUMMARY OF THE INVENTION

The present invention is directed to the discovery that the symptoms of neuropathic conditions including, but not limited to those symptoms associated with diabetes which may be effectively treated by administration of very low levels of anti-glutamic acid decarboxylase (anti-GAD) antibodies. Specifically, the antibodies may be administered in one or in multiple dosages, but the sum of antibodies administered in any 24 hour period (or daily period) is less than 10 mg each of anti-GAD, with preferred daily dosages being less than 1.0 mg and more preferably less than 0.1 mg.

While the antibody may be monoclonal or polyclonal, it is preferably monoclonal according to one aspect of the invention. The antibody may be administered by a variety of manners but is preferably administered subcutaneously and orally. Suitable methods of oral administration include oral drench and sublingual administration. According to another aspect of the invention the antibody is administered in an enterically protected form.

The invention provides methods for alleviating symptoms of neuropathic disorders by administering anti-glutamic acid decarboxylase (anti-GAD) antibody. Specifically, the invention provides methods for alleviating symptoms of a neuropathic condition such as autism, multiple sclerosis, Huntington's disease, Parkinson's disease, attention deficit disorder, diabetes neuropathy, and pain neuropathy following chemotherapy by administering to a patient in need thereof, anti-glutamic acid decarboxylase (anti-GAD) antibody in an amount effective to treat one or more symptoms of the neuropathic condition.

Methods of the invention comprise administration to a patient suffering from a neuropathic disorders such as autism, multiple sclerosis, Huntington's disease, Parkinson's disease, attention deficit disorder, diabetes neuropathy, and pain neuropathy following chemotherapy an effective amount of anti-glutamic acid decarboxylase (anti-GAD) antibody. The anti-glutamic acid decarboxylase is preferably administered in an amount ranging from about $1\times10^{-1}$ to $1\times10^{-6}$ microgram ($\mu$g) per day and is preferable formulated in a liquid vehicle and provided at a concentration of approximately $2\times10^{-2}$ $\mu$g as a single drop. A single drop of anti-glutamic acid decarboxylase antibody is within the range of $1\times10^{-2}$ to $1\times10^{-4}$ micrograms ($\mu$g). More preferably, a drop of anti-glutamic acid decarboxylase antibody is in the amount of $1.2\times10^{-3}$ micrograms ($\mu$g) per drop. The anti-glutamic acid decarboxylase antibody is more preferably administered in an amount ranging from about $1\times10^{-5}$ to $1\times10^{-2}$ microgram ($\mu$g) or from $1\times10^{-4}$ to $1\times10^{-2}$ $\mu$g or about $1\times10^{-3}$ $\mu$g per day. A preferred route of administration is sublingual, but other routes, such as bucal, oral drench, subcutaneous, intradermal, and intravenous, are expected to work.

The invention also provides methods for treating the symptoms of diabetes comprising the method of administering an effective amount of a combination of an antibody directed against GAD. The term "effective amounts of an antibody" is used herein to describe the amount of antibody administered to a subject to result in the reduction or elimination of the pathogenic autoimmune response associated with the onset of diabetes, thereby alleviating symptoms of diabetes. Preferred amounts of anti-GAD and anti-insulin antibodies for use according to the disclosed method are less than 1.0 mg of anti-GAD antibodies, and more preferably less than 0.5 mg of anti-GAD antibodies. A still more preferred daily dosage ranges from $1\times10^{-6}$ to $1\times10^{-2}$ mg of anti-GAD antibodies. An even more preferred daily dosage ranges from $1\times10^{-5}$ to $1\times10^{-3}$ mg of anti-GAD antibodies.

The invention also provides methods patients suffering for neuropathic disorders such as autism, multiple sclerosis, Huntington's disease, Parkinson's disease, attention deficit disorder, diabetes neuropathy, and pain neuropathy following chemotherapy comprising the method of administering an effective amount of anti-glutamic acid decarboxylase (anti-GAD) antibodies against GAD-65 or GAD-67. The anti-GAD antibodies can be directed against either GAD-65 or GAD-67 alone or in combination.

The invention also provides pharmaceutical compositions for administration to subjects for treatment of the symptoms of neuropathic conditions such as diabetic neuropathy, Huntington's disease, Parkinson's disease, autism, multiple sclerosis, attention deficit disorder (ADD), and pain neuropathy after chemotherapy, comprising a dosage unit of less than 1.0 mg of anti-GAD antibodies and preferably less than 1.0 $\mu$g of anti-GAD antibody. A still more preferred dosage unit is less than 0.5 $\mu$g of anti-GAD antibodies, and more preferably less than 0.1 $\mu$g of anti-GAD antibodies. A still more preferred dosage unit ranges from $1\times10^{-6}$ to $1\times10^{-2}$ $\mu$g of anti-GAD antibodies with dosage unit ranges of $1\times10^{-5}$ to $1\times10^{-2}$ $\mu$g or from $1\times10^{-4}$ to $1\times10^{-2}$ $\mu$g or about $1\times10^{-3}$ $\mu$g of anti-GAD antibodies being more preferred.

The invention also provides pharmaceutical compositions for administration to patients for treatment of symptoms of patients suffering from neuropathic disorders such as autism, multiple sclerosis, Huntington's disease, Parkinson's disease, attention deficit disorder, diabetes neuropathy, and pain neuropathy following chemotherapy comprising an effective amount of anti-glutamic acid decarboxylase (anti-GAD) antibodies against GAD-65 or GAD-67. The anti-GAD antibodies can be directed against either GAD-65 or GAD-67 alone or in combination.

DETAILED DESCRIPTION

The methods and compositions described herein relate to low levels of antibodies specific for the autoantigens of pancreatic beta cells that can reduce or eliminate the pathological consequences caused by the autoimmune response against the pancreatic beta cells. The mechanism by which this is accomplished is not completely understood and is the focus of ongoing research. Without intending to be bound by any particular theory of the invention, it is thought that the low levels of the antibodies specific for the autoantigens are able to prevent the pathogenic cascade that results from the destruction of the autoantigens by the immune system, possibly by redirecting the host immune system or by providing a negative feedback to prevent further autoimmune response. Particularly, the use of antibodies against GAD and insulin can be used as a systemic signal to specifically inhibit the body's aberrant, pathogenic response to the autoimmune response against GAD and insulin. In addition to the use of the disclosed method to alleviate symptoms of diabetes, it is further contemplated that practice of the methods disclosed herein will prove useful in the prevention of diabetes.

Symptoms of diabetes which can be treated according to the methods of the invention include elevated blood sugar level, elevated hemoglobin A1c level, neuropathy, retinopathy, ketoacidosis, and glycosuria. With respect to blood sugar levels, normal levels are<140 mg/dl and diabetic levels are considered to be levels>140 mg/dl.

The present invention also provides methods for treating patients with symptoms of autism by sublingual, or subcutaneously administering a small amount of anti-GAD antibody. Methods of the invention are also useful for treating, but not limited to, the symptoms of autism. In those cases, methods of the invention allow an autism patient to increase their attention span, sustain a conversation, develop language skills, communicate with words, socially interact, decrease repetitive body movements, decrease tantrums, expand interests, reduce preservation, reduce aggression to others or self, and increase social skills.

The present invention also provides methods for treating patients with symptoms of multiple sclerosis by sublingual or subcutaneous administration of a small amount of anti-GAD antibody. Methods of the invention are also useful for treating, but are not limited to, the symptoms of multiple sclerosis. In those cases, methods of the invention control or alleviate weakness of one or more extremities, paralysis of one or more extremities, tremors of one or more extremities, muscle spasticity, muscle atrophy, dysfunctional movement beginning in the legs, numbness, tingling, facial pain, loss of vision, double vision, eye discomfort, rapid eye movements, decreased coordination, loss of balance, dizziness, vertigo, urinary hesitancy, strong urge to urinate, frequent need to urinate, decreased memory, decreased spontaneity, decreased judgment, loss of ability to think abstractly, depression, decreased attention span, slurred speech, and fatigue.

The present invention also provides methods for treating patients with symptoms of Huntington's disease by sublingual or subcutaneous administration of a small amount of anti-GAD antibody. Methods of the invention are also useful for treating, but are not limited to, the symptoms of Huntington's disease. In those cases, methods of the invention control or alleviate the symptoms of irritability, restlessness, antisocial behavior, psychosis, paranoia, hallucinations, facial movements, progressive dementia, loss of memory, loss of judgment, speech changes, loss of other functions, personality changes, disorientation and confusion, unsteady gait, abnormal (choreiform) movements including jerking movements of the arms, legs, face, and trunk, speech impairment, anxiety, stress, tension and difficulty in swallowing that are associated with Huntington's disease.

The present invention also provides methods for treating patients with symptoms of Parkinson's disease by sublingual or subcutaneous administration of a small amount of anti-GAD antibody. Methods of the invention are also useful for treating, but are not limited to, the symptoms of Parkinson's disease. In those cases, methods of the invention control or alleviate the symptoms of muscle rigidity, loss of balance, shuffling walk, slow movements, difficulty beginning to walk, freezing of movement, muscle aches, shaking and tremors, changes in facial expression, voice/speech changes, loss of fine motor skills, frequent falls, and decline in intellectual function associated with Parkinson's disease.

The present invention also provides methods for treating patients with symptoms of pain neuropathy that is associated with chemotherapy by sublingual or subcutaneous administration of a small amount of anti-GAD antibody. Methods of the invention are useful for alleviating such pain associated with chemotherapy treatment.

The present invention also provides methods for treating various anxiety disorders by topically, sublingually, or subcutaneously administering to humans a small amount of anti-GAD antibody. These methods are also useful for treating panic disorders, and agoraphobia including, but not limited to, those involving shortness of breath, dizziness, palpitations, trembling, sweating, choking, nausea, chest pain, hot flashes or chills, fear of dying, fear of losing control, numbness, fear of going insane, feelings of detachment, feelings of helplessness, and avoidance of crowds, especially if escape or assistances is not immediately available. Other disorders subject to therapeutic treatment using anti-GAD antibody include attention deficit disorder (ADD) and obsessive/compulsive behavior.

Antibodies of the invention can be produced using any method well known and routinely practiced in the art. Such antibodies include monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide of the invention. A preferred anti-GAD antibody and anti-insulin antibody is available from Chemicon International Inc., Temecula, Calif.

The invention also provides a pharmaceutical composition for administering to a subject or patient for alleviating symptoms of a neuropathic condition selected from a group consisting of neuropathy diabetes, Huntington's disease, Parkinson's disease, autism, multiple sclerosis, attention deficit disorder (ADD), and pain neuropathy after chemotherapy, wherein the anti-GAD is in an amount effective to treat one or more symptoms of said psychological condition. An effective dosage comprises a dosage unit of less than 1.0 mg of anti-GAD antibodies and preferably less than 1.0 $\mu$g of anti-GAD antibody. A still more preferred dosage unit is less than 0.5 $\mu$g of anti-GAD antibodies, and more preferably less than 0.1 $\mu$g of anti-GAD antibodies. A still more preferred dosage unit ranges from $1\times10^{-6}$ to $1\times10^{-2}$ $\mu$g of anti-GAD antibodies with dosage unit ranges of $1\times10^{-5}$ to $1\times10^{-2}$ $\mu$g or from $1\times10^{-4}$ to $1\times10^{-2}$ $\mu$g or about $1\times10^{-3}$ $\mu$g of anti-GAD antibodies being more preferred. The anti-GAD antibodies can be directed against GAD-65 or GAD-67 alone or in combination of each other. The following examples are illustrative and are not intended to limit either the scope or spirit of the invention.

EXAMPLES

Example I

A male patient, who suffered uncontrolled lower limb pain associated with diabetes (diabetes neuropathy), as diagnosed by his physician, had been treated with a wide range of analgesics and narcotics with only limited relief over a two year period. Patient was then placed on treatments of one sublingual drop (0.05 ml)(0.006 $\mu$g/drop) of anti-GAD (Ab directed against combination of GAD-65 and GAD-67) 3–4 times daily. During three months of treatment, patient experienced resolution of his pain and has been able to discontinue narcotic treatments and was able to reduce treatment dosages to one sublingual drop per day.

Example II

A 60-year old male who suffered from advanced Parkinson's, as diagnosed by his physician, was treated with a sublingual dose of one drop (0.05 ml)(0.0012 $\mu$g/drop) of anti-GAD (Ab directed against GAD-67) 3–4 times daily. After 9–10 weeks of treatment, patient experienced improved mobility, ability to speak, and positive attitude. No adverse effects of the anti-GAD treatment were experienced by the patient.

Example III

A patient, who suffered from Parkinson's disease, as diagnosed by his physician, was treated with a sublingual dose of one drop (0.05 ml)(0.0012 $\mu$g/drop) of anti-GAD (Ab directed against GAD-67) 3–4 times daily. After 4 weeks of treatment, patient experienced complete resolution of lower extremity tremors and elimination of incidents of falling due to the Parkinson tremors. In addition, the patient experiences a 40% improvement in tremors of the upper extremities. No adverse effects of the anti-GAD treatment were experienced by the patient and the patient was able to reduce administration to one drop daily.

Example IV

A 28-year old male who suffered from autism, as diagnosed by his physician, was treated with a sublingual dose of one drop (0.05 ml)(0.006 µg/drop) of anti-GAD (Ab directed against GAD-67)once daily. Upon initiation of treatment, patient experienced improved tolerance to foods permitting a wider choice of diet, decreased anxiety, improved sleep patterns, improved bladder control, improved cognition and attention, and increased efforts to speak. Therefore, the anti-GAD treatments appear to improve both neurological and auto-immunological disorders associated with autism. No adverse affects of the anti-GAD treatment was experienced by the patient. In fact, patient had developed allergies to many other treatment regiments for his autism.

Example V

A 9-year old male who suffered from autism, as diagnosed by his physician, was treated with a sublingual dose of one drop (0.05 ml)(0.006 µg/drop) of anti-GAD (Ab directed against GAD-67)once daily. Upon treatment for four weeks, patient experienced improved school work, greater attention span to teachers and parents, appropriately entertained him, and had a more controlled behavioral pattern.

Example VI

A 54-year old male who suffered from multiple sclerosis for over 30 years was treated with a sublingual dose of one drop (0.05 ml)(0.0012 µg/drop) of anti-GAD(Ab directed against GAD-67) 3 times daily for several months. Upon initiation of treatment, patient experienced feeling in his lower extremities, specifically patient could feel the carpet with his feet. Physical capabilities have improved as well. Patient was able to walk unassisted for at least 100 yards. The patient also experienced improved bladder function and vision and reduced dosage rate to one drop daily.

Example VII

A 45-year old female patient who suffered from multiple sclerosis for over 20 years was treated with a sublingual dose of one drop (0.05 ml)(0.0012 µg/drop) of anti-GAD (Ab directed against GAD-67) 2–3 times daily. Upon initiation of treatment, patient experienced improved vision, less fatigue, sleeps through the night, and a decreased numbness in the mid-calf down bilaterally thus improving his overall balance.

Example VIII

A 53-year old female patient who sufferance from multiple sclerosis was treated with one sublingual drop (0.05 ml)(0.0012 µg/drop) of anti-GAD (Ab directed against GAD-67) twice daily. After one month of treatment, patient experienced less spasms and tremors, a moderate increase in energy level, and a return of her balance.

Example IX

A middle age female patient diagnosed with anxiety disorder and obsessive/compulsive behavior by her physician was treated with one sublingual drop (0.05 ml)(0.006 µg/drop) of anti-GAD (Ab directed against GAD-67 twice daily over a two week period. During treatment period, patient was able to control anger and anxiety. These feelings, however, returned after administration of the anti-GAD has ended. Patient continued to be administer anti-GAD, but reduced the dosage to one drop at an "at need basis."

Example X

According to this example, a 45 year old female diagnosed with insulin-dependent diabetes was treated with low level antibodies (Abs directed against combination of GAD-65 and GAD-67). The subject was determined to have a hemoglobin A1C level of 11%, which is typically at a level of 4–6% in non-diabetic individuals. The subject experienced neuropathy characterized by numbness and poor circulation as determined by the subject in response to a tuning fork test. The subject underwent antibody therapy by sublingual administration, via drops, twice daily of one dose of anti-GAD ($8\times10^{-4}$ mg) and anti-insulin antibodies ($4\times10^{-4}$ mg). The antibodies used in this example are the same as that used above in Example I. The subject was tested for hemoglobin A1C levels after 2 weeks of therapy and the levels were reduced to 7%. The subject was free from any other therapies during the low level antibody therapy. After one week the subject experienced a disappearance of neuropathy in the subject's lower extremities. The low level antibody treatment was stopped and the subject's previously experienced neuropathy returned after approximately one week.

Example XI

According to this example, a 42 year old female with a 20 year history of diabetes mellitus was treated with low level antibodies. The subject was treated with antibody therapy by sublingual administration in the form of 1 drop (or dose), 4×per day. Each dose contained $8\times10^{-4}$ mg of anti-GAD and $4\times10^{-4}$ mg of anti-insulin antibodies. The antibodies used in this example are the same as that used above in Example I. After approximately one week, the subject experienced an abatement of pain from diabetic neuropathy and a reduction in blood sugar levels. Following a one week period in which the subject experiences no pain, the subject was discontinued from low level antibody treatment. The discontinuation resulted in reoccurrence of diabetic neuropathy and elevated blood sugar levels, which were the symptoms experience by the subject prior to low level antibody treatment. Subsequently, the subject was, again, treated with low level antibody therapy, which resulted in abatement of pain from diabetic neuropathy and a reduction in blood sugar levels similar to the result from the initial therapy with low level antibodies.

Example XII

According to this example, a white male diagnosed with diabetes was treated with low level antibodies. The subject was treated with antibody therapy by sublingual administration in the form of 1 drop (or dose), 2×per day. Each dose contained $8\times10^{-4}$ mg of anti-GAD (Ab directed against combination of GAD-65 and GAD-67) and $4\times10^{-4}$ mg of anti-insulin antibodies. The antibodies used in this example are the same as that used above in Example I. After approximately eight weeks the subject experienced a reduction in diabetic neuropathy of approximately 60%. This reduction in diabetic neuropathy was determined by having the patient assess the sensations resulting from a tuning fork on the subject's lower extremities just prior to treatment and after the eight weeks of treatment. Additionally, the subject experienced a loss in weight (approximately 12 lbs), increased energy and a reduction in levels of blood sugar of about 40 mg/dl.

Example XIII

A 55-year old female patient who suffers pain neuropathy due to her recovery efforts from chemotherapy and surgery to the mandible jaw bone in efforts to treat osteocarcinoma. Patient was treated with numerous narcotics to control the pain but patient continues to suffer despite prescribed narcotics. Patient was administered a sublingual dosage of one drop (0.05 ml)(0.0012 µg/drop) of anti-GAD (Ab directed against GAD-67) 3 to 4 times daily. After 2 weeks of treatment, patient experienced complete elimination of the pain neuropathy and reduced the dosage of anti-GAD to one drop daily.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of alleviating symptoms of neuropathic conditions comprising the step of administering anti-glutamic acid decarboxylase (anti-GAD) antibody in an amount effective to alleviate symptoms of said neuropathic condition.

2. The method of claim 1, wherein the neuropathic conditions are selected from the group consisting of autism, multiple sclerosis, Parkinson's disease, attention deficit disorder, diabetic neuropathy and pain neuropathy associated with chemotherapy treatment.

3. The method of claim 1 wherein the anti-GAD antibodies are monoclonal antibodies.

4. The method of claim 1 wherein the administration step is oral.

5. The method of claim 4 wherein the administration step is sublingual.

6. The method of claim 4 wherein the anti-GAD antibodies are administered in an enterically protected form.

7. The method of claim 1 wherein the administration step is by injection.

8. The method of claim 7 wherein the administration step is by subcutaneous injection.

9. The method of claim 1 comprising less than 1.0 mg of anti-GAD antibodies.

10. The method of claim 9 comprising less than 1.0 µg of anti-GAD antibodies.

11. The method of claim 9 comprising from $1 \times 10^{-6}$ to $1 \times 10^{-2}$ µg of anti-GAD antibodies.

12. The method of claim 9 comprising from $1 \times 10^{-5}$ to $1 \times 10^{-2}$ µg of anti-GAD antibodies.

13. The method of claim 1, wherein the anti-GAD antibody is specific for GAD-65.

14. The method of claim 1, wherein the anti-GAD antibody is specific for GAD-67.

15. A pharmaceutical composition for administration to a subject for alleviating symptoms of neuropathic conditions comprising less than 1.0 mg of anti-GAD antibodies.

16. The pharmaceutical composition of claim 15 comprising less than 0.1 µg of anti-GAD antibodies.

17. The pharmaceutical composition of claim 15 comprising from $1 \times 10^{-6}$ to $1 \times 10^{-2}$ µg of anti-GAD antibodies.

18. The pharmaceutical composition of claim 15 comprising from $1 \times 10^{-5}$ to $1 \times 10^{-2}$ µg of anti-GAD antibodies.

19. The pharmaceutical composition of claim 15, wherein the antibodies are specific for GAD-65.

20. The pharmaceutical composition of claim 15, wherein the antibodies are specific for GAD-67.

* * * * *